US009504809B2

(12) United States Patent
Bo

(10) Patent No.: US 9,504,809 B2
(45) Date of Patent: Nov. 29, 2016

(54) CATHETER WITH A BALLOON

(75) Inventor: Nielsen Rud Bo, Allerød (DK)

(73) Assignee: Coloplast A/S, Humlebaek (DK)

( * ) Notice: Subject to any disclaimer, the term of this patent is extended or adjusted under 35 U.S.C. 154(b) by 20 days.

(21) Appl. No.: 14/126,871

(22) PCT Filed: Jun. 29, 2012

(86) PCT No.: PCT/DK2012/050231
§ 371 (c)(1),
(2), (4) Date: Dec. 17, 2013

(87) PCT Pub. No.: WO2013/004236
PCT Pub. Date: Jan. 10, 2013

(65) Prior Publication Data
US 2014/0121596 A1 May 1, 2014

(30) Foreign Application Priority Data
Jul. 1, 2011 (DK) .................................. 2011 70354
Oct. 31, 2011 (DK) .................................. 2011 70589

(51) Int. Cl.
A61M 25/10 (2013.01)
A61M 27/00 (2006.01)
A61M 25/00 (2006.01)

(52) U.S. Cl.
CPC .......... *A61M 27/00* (2013.01); *A61M 25/0043* (2013.01); *A61M 25/10* (2013.01); *A61M 25/0017* (2013.01); *A61M 2025/006* (2013.01)

(58) Field of Classification Search
CPC ........... A61M 25/10; A61M 25/1002; A61M 25/10; A61M 2025/1043; A61M 2025/1095; A61M 2025/1097; A61M 27/00; A61M 25/0041; A61M 27/008; A61M 2210/1089; A61M 2210/1078; A61F 2/04

USPC ........................................................ 604/96.01
See application file for complete search history.

(56) References Cited

U.S. PATENT DOCUMENTS

| 2,693,191 A * | 11/1954 | Raiche | A61M 25/1011 604/101.05 |
| 3,924,634 A * | 12/1975 | Taylor | A61M 25/1002 604/100.01 |
| 4,259,960 A * | 4/1981 | Taylor | A61M 25/10 604/102.03 |
| 4,342,316 A * | 8/1982 | Rosenberg | A61M 25/1002 604/103 |
| 4,762,128 A | 8/1988 | Rosenbluth | |
| 5,195,970 A * | 3/1993 | Gahara | A61L 29/04 604/103.08 |
| 5,593,394 A | 1/1997 | Kanesaka | |
| 5,645,528 A * | 7/1997 | Thome | A61M 25/001 604/113 |
| 5,882,347 A * | 3/1999 | Mouris-Laan | A61M 25/0023 604/103.09 |
| 5,944,726 A | 8/1999 | Lorentzen Cornelius | |
| 6,033,379 A | 3/2000 | Bocheff | |

(Continued)

FOREIGN PATENT DOCUMENTS

| CA | 1117839 A1 | 2/1982 |
| DE | 10215462 A1 | 10/2003 |

(Continued)

Primary Examiner — Aarti B Berdichevsky
Assistant Examiner — Jenna Zhang
(74) Attorney, Agent, or Firm — Coloplast Corp., Coloplast A/S; Nick Baumann

(57) ABSTRACT

A catheter with a balloon element is provided with ribs under the balloon element so as to prevent the balloon from being attached to the shaft of the catheter to an extent where the balloon is difficult to inflate. The number of ribs can be any number above 3, but 6 to 16 ribs are preferred.

20 Claims, 3 Drawing Sheets

(56) References Cited

U.S. PATENT DOCUMENTS

| | | | |
|---|---|---|---|
| 6,210,367 B1* | 4/2001 | Carr | A61B 18/18 604/114 |
| 6,514,228 B1* | 2/2003 | Hamilton | A61F 2/958 604/102.01 |
| 7,118,987 B2 | 10/2006 | Lu | |
| 7,306,616 B2 | 12/2007 | Eidenschink | |
| 2004/0059292 A1 | 3/2004 | Hisamatsu et al. | |
| 2004/0086674 A1 | 5/2004 | Holman | |
| 2005/0177104 A1* | 8/2005 | Conway | A61M 25/10 604/96.01 |
| 2007/0005092 A1 | 1/2007 | Wise | |
| 2008/0249464 A1* | 10/2008 | Spencer | A61M 25/1002 604/103 |
| 2009/0018500 A1 | 1/2009 | Carter | |
| 2010/0191183 A1 | 7/2010 | Guldager | |

FOREIGN PATENT DOCUMENTS

| | | |
|---|---|---|
| EP | 0145505 A2 | 6/1985 |
| EP | 1556125 B1 | 8/2006 |
| WO | 9626748 A2 | 9/1996 |
| WO | 0051674 A1 | 9/2000 |
| WO | 2007005234 A1 | 1/2007 |

* cited by examiner

CATHETER WITH A BALLOON

The invention relates to a catheter with a balloon. The invention also relates to an indwelling catheter with a balloon and a rectal catheter with a balloon.

BACKGROUND

Foley-type catheters are tube-like devices that are used to drain urine from a user's bladder. Foley catheters are inserted through the urethra and are typically held in place with an inflatable balloon. The balloon is in a deflated position when the catheter is inserted at first. Once the catheter is in the proper position, the balloon is inflated with a fluid. The diameter of the inflated balloon is larger than the diameter of the urethra and thereby prevents the catheter from falling out of the bladder. Foley catheters are also known as "indwelling" catheters because they are designed to be left in place for longer periods of time, typically several days.

Other types of catheters or insertion devices also comprise a tube-like element and a balloon fixed to the outside surface of the catheter. An example of this is rectal catheters, which are typically used in connection with anal irrigation. Anal irrigation is often used to stimulate the peristaltic function of the intestines and thus reduce constipation. Paralysed persons suffering from e.g. spinal cord injuries, spina bifida or multiple sclerosis may suffer from decreased peristaltic function and thereby reduced function of the bowel system. In connection with anal irrigation, an irrigation liquid (typically water) flows into the rectum through a rectal catheter, which is held in place in the rectum by an inflated balloon.

SUMMARY OF THE INVENTION

The invention relates to a catheter with a balloon element. The catheter has a shaft provided with longitudinal ribs, which assist in minimizing the contact area between the uninflated balloon element and the shaft. This may be an advantage, because otherwise the balloon element may tend to adhere to the shaft during storage of the finished catheter.

DETAILED DESCRIPTION OF THE INVENTION

In a first aspect, the invention relates to a catheter comprising
 a shaft comprising a tubular element extending from a proximal end to a distal end
 a balloon element fitted on the shaft
wherein the shaft is provided with ribs in the longitudinal direction on an outer surface of the tubular element so that the ribs are positioned under the balloon element.

Providing ribs on the catheter shaft under the balloon element has the effect that the balloon will have a smaller contact area with the shaft prior to inflation. If the ribs are not present, a situation may occur where the balloon has attached itself to the surface of the shaft and thus is substantially prevented from being inflated properly.

The balloon material may contain a substantial amount of oil. This oil may increase the tack and hence the tendency of the balloon element to adhere to the outer surface of the shaft. Therefore, providing ribs and thus decreasing the contact area between the balloon element and the shaft minimises the risk of adhesion. The present inventors have realized that the adhesion or tack of the balloon element to the shaft surface is a major factor in the peak pressure during balloon inflation. That is, the initial pressure needed to get a balloon inflated the first few percent is typically higher than the pressure needed to inflate the rest of the balloon. By reducing the adhesion or tack or contact between the balloon element and the shaft surface, the initial pressure (the peak pressure) is reduced. The user (typically in wheel chair) will be hesitant to apply too much pressure to an anally placed device. Not only due to the fear of the balloon exploding due to the high pressure, but also the often limited muscle force makes provision of high peak pressure hard. Having limited the peak pressure, due to the ribs, enables balloon catheters to be inflated without fear and with ease.

Longitudinally spaced ribs provide for gentle insertion and easy inflation of the balloon without any additional means. Transverse ribs may be uncomfortable during insertion because they are perpendicular to the direction of insertion.

In the following, whenever referring to the proximal end of an element of the invention, the referral is to the end adapted for insertion. Whenever referring to the distal end of an element, the referral is to the end opposite the insertion end. In other words, the proximal end is the end closest to the tip of the catheter. The distal end is the opposite end, i.e. the end closest to the handle.

The longitudinal direction is the direction from the distal to the proximal end. The transverse direction is the direction perpendicular to the longitudinal direction, which corresponds to the direction across the shaft of the catheter.

The catheter according to this invention typically comprises a cylindrical shaft extending from the distal end to the proximal end where it terminates in a rounded tip. The tip may in an embodiment be half-spherically shaped.

The catheter may be provided with a connector part in the distal end so as to enable coupling of the catheter with tubing. This connector is in its simplest form merely a flared end of the tubular part, which provides a friction fit with an oppositely flared end on a piece of tubing. The connector may also be a more complex element allowing for connection to a double lumen tube, for example a connector as described in European Patent no. EP1556125B1.

The catheter may be provided with eyelets near the proximal end. These eyelets function as holes for letting irrigation liquid pass into the intestines, when the catheter is used as a rectal catheter. The eyelets function as drainage holes for draining urine, when the catheter is used as an indwelling urinary catheter.

The catheter according to the invention comprises one or more liquid channel(s) extending through the catheter from the distal end to the proximal end or to eyelets near the proximal end.

The one or more liquid channels may vary in size depending on whether the catheter is used for insertion in the urethra or in the rectum.

For a rectal catheter the liquid channel(s) are used for instillation of the irrigation liquid. For an indwelling urinary catheter the liquid channel(s) are used for the excretion of urine and, optionally, for instillation of liquid in the bladder. The catheter further comprises a balloon channel extending from the distal end and through the shaft until it terminates in one or more inflation outlets provided under the balloon element. Thereby, the balloon element may be inflated by blowing fluid through the balloon channel from the distal end of the catheter. The balloon can also be deflated through the balloon channel after the completion of catheterization.

In the context of this application, a fluid is defined here as either air or a liquid, such as water.

The materials for the catheter and the balloon element are preferably thermoplastic, elastomeric materials, for example materials like Styrene-ethylene-butylene-styrene, SEBS. The materials may be selected to be weldable to each other. For the catheter material the Shore A value may be between 30 and 80 Shore A, for example approximately 70 Shore A.

An embodiment of this invention relates to a catheter as described above, which is adapted for use as a Foley catheter. A Foley catheter may be used as an indwelling catheter, where the balloon element is used to hold the catheter in place inside the bladder, so that urine may flow out through the catheter and into a collection bag. A Foley catheter is typically between 150 and 400 mm long depending on whether it is to be used for females or males. Such a catheter is usually in a size between 8 FR and 18 FR depending on the size of the urethra.

A Foley catheter is inserted through the urethra until the tip, the drainage holes (eyelets) and the balloon element are inside the bladder. In this position the balloon element is inflated so as to prevent the catheter from falling out. The catheter may be left inside the urethra for several days or even as long as up to two weeks or more. During the use, the Foley catheter continuously drains urine from the bladder and through the urethra to a collecting bag.

When the catheter is a Foley catheter, the eyelets function as inlets to the drainage channel in the catheter. Thereby, urine from the bladder may enter into the catheter through the eyelets and be drained through the drainage channel to a collecting bag.

An anal catheter typically comprises a tip part at the proximal end and a connector part at the distal end. The tip part may be in the form of a cylindrical element having a rounded end and including eyelets for instillation of the irrigation liquid. The connector part includes the connector for connecting the catheter to a tube and thus defines the inlet to the catheter.

The anal catheter or probe may be in the form of a generally longitudinal, cylindrical body. The cylindrical body may be provided with a coating so as to make the insertion easier.

The outer diameter of such a catheter is typically about 8-16 mm, for example 10 mm. The length is about 70-200 mm, for example about 150 mm.

The longitudinal direction or the length direction of the catheter is defined as the direction extending from the proximal to the distal part or vice versa, that is, the direction along the cylindrical body. The transverse direction of the catheter is defined as any direction perpendicular to the longitudinal direction.

An anal catheter is used to provide anal irrigation. Therefore it requires a water channel allowing a certain flow of liquid through it. Tests have shown that a diameter of approximately 3-7 mm, for example 4.3 mm provides an adequate flow. Furthermore, an anal catheter with an inflatable balloon may be provided with a balloon channel allowing a certain flow so as to easily inflate the balloon. An adequate diameter of the balloon channel is approximately 1-4 mm such as 2 mm in diameter.

When the catheter is an anal catheter, the eyelets are outlets for the water channel so that it is possible for irrigation liquid to enter through the catheter and exit it through the water channel.

Another aspect of the invention relates to a rectal catheter comprising
 a shaft comprising a tubular element extending from a proximal end to a distal end
 a balloon element fitted on the shaft wherein the balloon is fitted in an attenuation in the catheter so that the balloon is within the outer boundary of the catheter.

This provides a catheter with a smooth outer surface.

The balloon element should be prevented from touching the catheter surface between the ribs. To achieve this, the height of the ribs (radially with respect to the shaft of the catheter) should be large enough to keep the balloon element distended over the surface between the ribs. This height depends on the number of ribs used. We have determined the optimal relationship between height of ribs and number of ribs used.

The relationship between the height, h, and number, n, of ribs is as follows: If the ribs are positioned equidistantly around the circumference of the catheter, their peaks define a polygon with the number of corners (and hence the number of sides) corresponding to the number of ribs. The peak of each rib defines the corners of the polygon, and the sides are delineated by the inner side of the balloon element, which is stretched across the ribs. In order to prevent the balloon element from touching the surface of the catheter in the troughs between the ribs, this polygon should be at least as large as the circumscribed polygon around the catheter (so that the catheter is the inscribed circle of the polygon). The circumscribed polygon and hence the height of the ribs can be determined by using simple geometry.

FIG. 4 of the drawings illustrates the principle for calculating the minimum height of the ribs, h. The angle $\alpha$ represents the angle between the ribs (in the figure 90° or $\pi/2$), and r is the radius of the catheter at the bottom of the troughs between the ribs, the bottom of the troughs will occur at the angle $\alpha/2$. Using simple trigonometry, h is determined in the following way:

$$\alpha = \frac{2\pi}{n} = \frac{360°}{n}$$

Where n is the number of ribs; n≥3.

$$\cos\frac{\alpha}{2} = \frac{r}{x} \Leftrightarrow x = \frac{r}{\cos\frac{\alpha}{2}}$$

$$h = x - r = \frac{r}{\cos\frac{\alpha}{2}} - r = r \cdot \left(\frac{1}{\cos\frac{\alpha}{2}} - 1\right)$$

This may also be expressed in the relation between angles in radians or degrees and number of ribs:

$$h = r \cdot \left(\frac{1}{\cos\frac{\pi}{n}} - 1\right) = r \cdot \left(\frac{1}{\cos\frac{180°}{n}} - 1\right)$$

Examples with an even number of ribs are given below, though an uneven number of ribs is equally possible:

Calculations of Height for Number of Ribs Between 4 and 30

The table below shows the minimum height of the ribs calculated for a catheter with a diameter at the ribs=8 mm (radius=4 mm) and number of ribs=4, 6, 8, 10, 12, 14, 16, 18, 20 and 30.

TABLE 1

| Number of ribs | angle between ribs degrees | height, h mm |
|---|---|---|
| 4 | 90 | 1.66 |
| 6 | 60 | 0.62 |
| 8 | 45 | 0.33 |
| 10 | 36 | 0.21 |
| 12 | 30 | 0.14 |
| 14 | 26 | 0.10 |
| 16 | 22.5 | 0.08 |
| 18 | 20 | 0.06 |
| 20 | 18 | 0.05 |
| 30 | 12 | 0.02 |

As can be seen from the table the use of 4 ribs will provide ribs of a height of more than 1 mm. For most uses, it would be undesirable to have such high ribs.

For a rectal catheter, the ribs and the balloon may be within the boundaries of the remaining part of the catheter, thus preventing the ribs and balloon from protruding from the general boundary of the catheter. In other words, the ribs and balloon may be provided at an attenuation of the catheter. Such a catheter is more comfortable to use.

A rectal catheter may for example be 10 mm in diameter and the balloon material may be 0.4-0.5 mm thick. Thus, if the balloon is 0.4 mm thick, then the diameter of the catheter at the attachment surfaces where the balloon is attached (e.g. welded) to the catheter should be 9.2 mm, leaving room for 2×0.4 mm balloon material.

The catheter must have room inside for the water channel and the balloon channel. Thus, the catheter must have a diameter of at least 8 mm to leave room inside for a 4-5 mm water channel and a 1-2 mm balloon channel. This leaves 1 mm in diameter for the ribs (=9 mm diameter at attachment surfaces minus 8 mm catheter minimum diameter). Thus, each rib can only reach maximum height of 0.5 mm if they are to be placed equidistantly. From the table above (Table 1), it appears that the number of ribs should be 8 or more to provide a height below 0.5 mm. In other words, the catheter may comprise two attenuations at the position of the balloon. A first attenuation may be provided between the outer surface of the catheter and the attachment surfaces to leave room for the balloon. A second attenuation may be provided between the attachment surfaces and the attenuated catheter surface at the balloon to leave room for ribs.

Table 2 below shows results of calculating the total contact area between the balloon and the ribs. This area should be as low as possible to minimise the migration of oil from the balloon.

The largest radius of curvature—and thus the largest possible contact length between the balloon and the ribs—occurs when the ribs describe an arc that is part of a circle.

As described above, and provided that the ribs are positioned equidistantly around the catheter, the balloon will be in contact with the ribs at the peak, p, of the ribs (corresponding to distance h from the periphery of the catheter) and a part of the circular arc defining the ribs. The balloon may also just touch the catheter in the troughs between the peaks, where it will describe a tangent to the circle defining the circumference of the catheter. The circular arc defining the ribs has a centre at the periphery of the catheter and a radius equal to the height, h, calculated as shown above. The part of the circular arc of the ribs, which is in contact with the balloon, can be calculated as follows and as shown in FIG. 5.

The tangent line at the troughs between the ribs (at angle α/2) will touch the circular arc at a first contact point p1 and at the peak, p. The angle between the tangent line and an extended radial line of the catheter will be (90−α/2), which is easily seen using a simple consideration of triangles. Likewise, a tangent line at the next trough (at angle 3α/2) will touch the circular arc at a second contact point p2 and at the peak p. Again the angle between the tangent line and an extended radial line of the catheter will be (90−α/2). Thus, the combined angle θ at the periphery of the circular arc will be:

$$\theta = \left(90 - \frac{\alpha}{2}\right) + \left(90 - \frac{\alpha}{2}\right) = 180 - \alpha$$

The lines from p to p1 and from p to p2 define chords of the circular arc and we wish to determine the length L of the arch between p1 and p2. It is well-known that the inscribed angle θ of a circle defined by two chords is half of the central angle 2θ that subtends the same arc on the circle. To determine L between p1 and p2 (highlighted in the figure), we have to use the angle, v, at the central part between p1, the centre and p2. This corresponds to 360−2θ. Thus v is determined as:

$$v = 360 - 2\theta = 360 - 2(180 - \alpha) = 2\alpha$$

Therefore the length at the arch L between p1 and p2 can be determined from the following:

$$\frac{L}{2\pi r} = \frac{v}{360} \Rightarrow L = \frac{v 2\pi r}{360}$$

Table 2 below shows calculations of L at each rib, of total contact length (L times number of ribs) and of total contact area provided that the length of the ribs are 24 mm.

TABLE 2

| Number of ribs | Length of curve at each rib [mm] | Total contact length mm | Total contact area mm² |
|---|---|---|---|
| 4 | 5.21 | 20.8 | 499.7 |
| 6 | 1.30 | 7.78 | 186.6 |
| 8 | 0.52 | 4.14 | 99.40 |
| 10 | 0.26 | 2.59 | 62.08 |
| 12 | 0.15 | 1.77 | 42.56 |
| 14 | 0.09 | 1.29 | 31.02 |
| 16 | 0.06 | 0.98 | 23.63 |
| 18 | 0.04 | 0.78 | 18.61 |
| 20 | 0.03 | 0.63 | 15.04 |
| 30 | 0.01 | 0.28 | 6.65 |

From the table it appears that adding more than 16 ribs only provide for a slight reduction in the total contact area, whereas providing less than 6 ribs will lead to an unacceptable increase in the total contact area.

Thus, in an embodiment of the invention, the number of ribs is between 6 and 16 and preferably 8.

In an embodiment of the invention, the ribs are rounded at the peaks in a circumferential direction around the catheter.

Rounding of the peaks may prevent the ribs from cutting into the balloon element and thus perforating it.

The peaks may be rounded so that the transverse cross-section of the ribs of the catheter forms part of a circular arc. Circular arc cross-sections will have the largest radius of curvature possible and thus the smallest curvature, which means that it will be less sharp than any other shape.

In one embodiment, the ribs are shorter than the distance between the attachment surfaces of the balloon. For example the distance between the end of a rib and the closest attachment surface may be approximately 0.5 mm. However, the distance should not be so large that the balloon element will touch the area between the rib and the closest attachment surface.

In an embodiment, the balloon channel has outlets in one end of the area between the attachment surfaces, and the ribs do not extend all the way to the attachment surface so that a gap is present between the end of the ribs and the closest attachment surface in this end.

Leaving a gap at the distal end may allow for an easy and quicker distribution of the fluid under the balloon element. This is because the fluid can flow circumferentially around the catheter and enter into the troughs between the ribs without having to inflate a single balloon element first. When the fluid has filled the troughs then the actual inflation starts. This provides for an even inflation of the balloon element.

Alternatively, the fluid outlets may be provided as one outlet in each trough.

There may be gaps in one end, in both ends or no gaps at all.

DETAILED DESCRIPTION OF THE DRAWING

Figure 1:
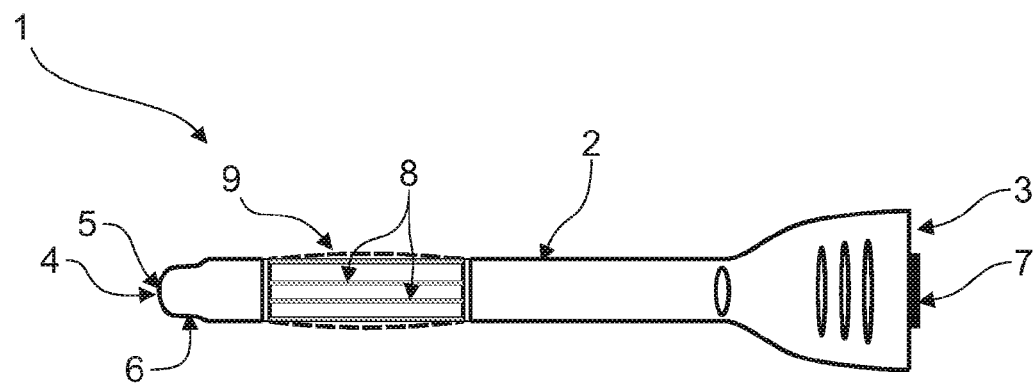
FIG. 1 illustrates a side-view of a catheter according to the invention.
Figure 2:
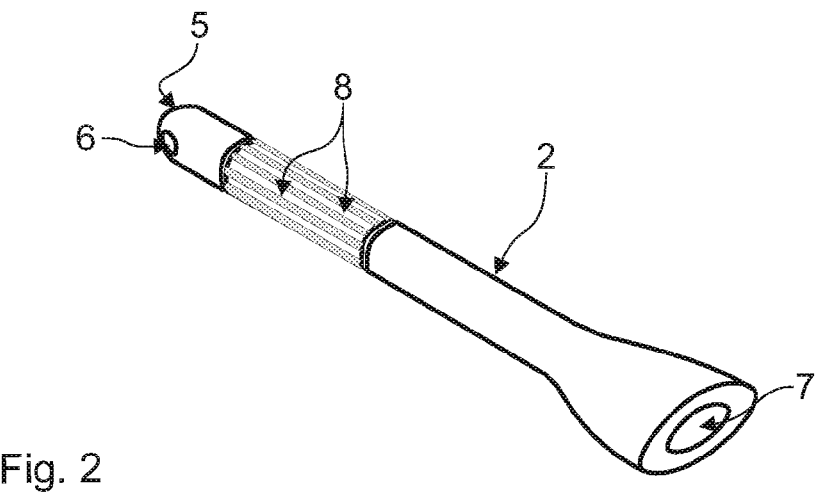
FIG. 2 illustrates a perspective view of a catheter according to the invention.
Figure 3:
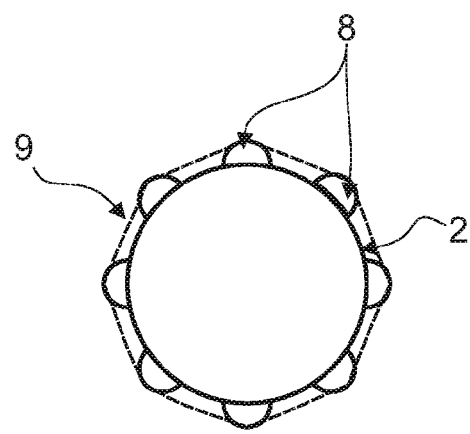
FIG. 3 illustrates a cross sectional view of a catheter according to the invention.

The catheter 1 illustrated in FIGS. 1 to 3 has a generally cylindrical shaft 2 extending from a distal end 3 to a proximal end 4. In the proximal end 4, the catheter is provided with a rounded tip 5 and eyelets 6. In the distal end 3, the catheter is provided with a connector part 7. The catheter is provided with ribs 8 at the shaft 2 where the balloon element 9 will be fitted in the finished catheter. The position of the balloon element 9 is only shown as dashed lines in FIGS. 1 and 3. Outlets from the balloon channel (not shown) may be positioned in the troughs between the ribs 8.

Figure 4:
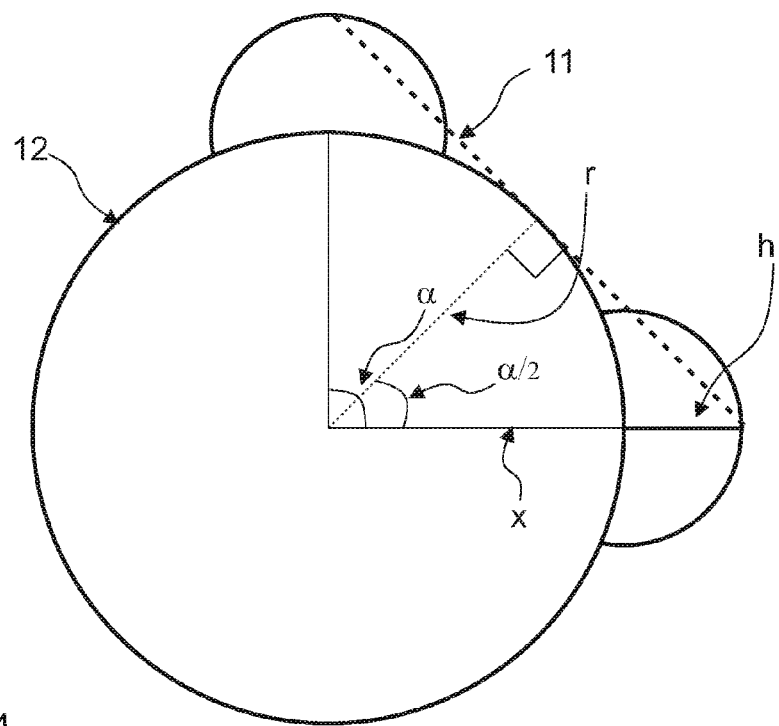
FIG. 4 illustrates calculation of the minimum height, h.
Figure 5:
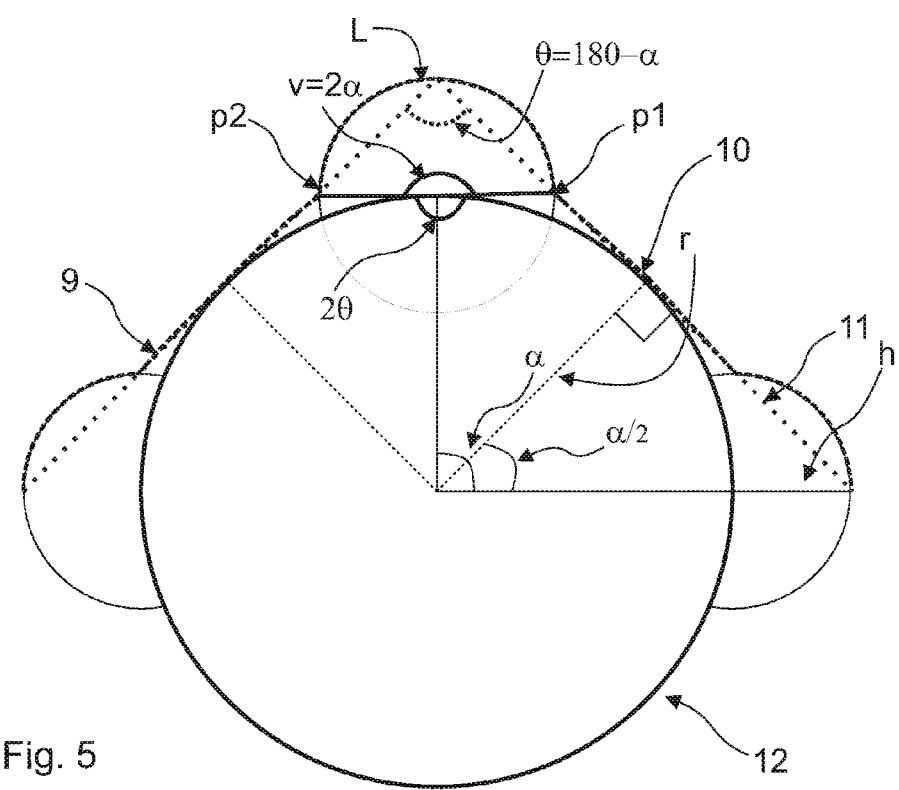
FIG. 5 illustrates calculation of the contact length, L, between the balloon element and a rib.

FIGS. 4 and 5 illustrate how the minimum height, h, of the ribs are determined and how the contact length between the balloon element 9 and the ribs 8 are determined.

α is the angle between two ribs 8 and α/2 determines the position of the touch point 10 of the balloon element at the trough between two ribs. The dashed line 11 indicates the tangent to the circle 12 describing the circumference of the catheter at the troughs. It appears from the figure that the length, x and thus the height, h, can be determined by simple trigonometry as it is explained above.

FIG. 5 illustrates how the balloon element 9 will touch the catheter ribs 8 at a length L between the points p1 and p2. The length L can be calculated as shown above. The angles θ and v appears from the figure. In FIG. 5 the dotted lines 11 illustrate the tangent lines to the circle 12 and the dashed line indicates the balloon element 9. Only part of the balloon element 9 is illustrated.

Figure 6:
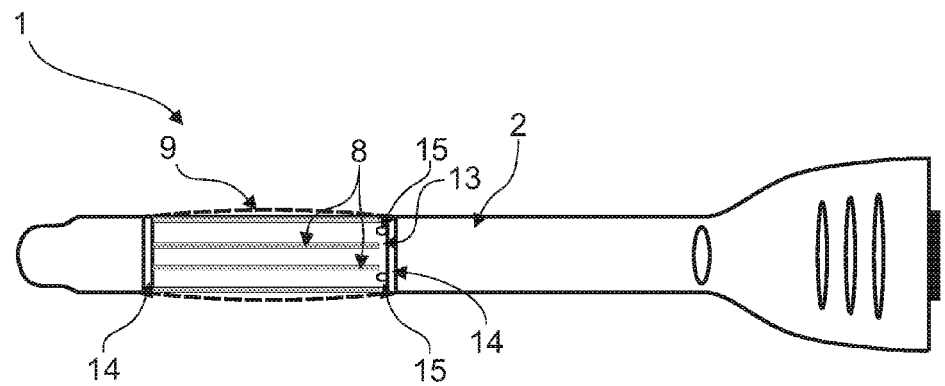
FIG. 6 illustrates gaps and outlets for the balloon channel at one end of the balloon area of the catheter.

FIG. 6 illustrates a catheter 1 having a gap 13 between the attachment surface 14 and the ribs 8. The outlets 15 from the balloon channel are positioned in this gap 13.

Figure 7:
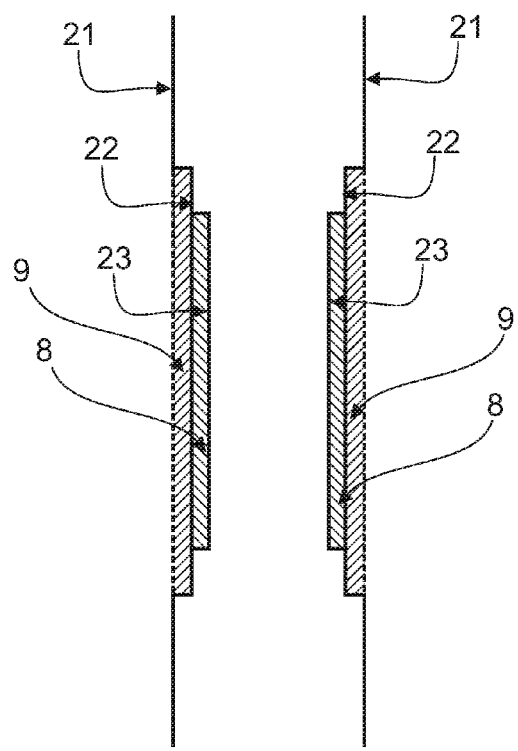
FIG. 7 illustrates a longitudinal cross-section of a part of a catheter according to the invention.

FIG. 7 illustrates a cross-section of a part of a catheter according to the invention. The balloon 9 is attached flush with the outer surface 21 of the catheter and on the outer surface of the ribs 8. The balloon is attached at an attachment surface 22 that is attenuated with respect to the outer surface 21 of the catheter. The ribs 8 are attached at an attenuated catheter surface 23 that is attenuated with respect to the attachment surface 22.

The invention claimed is:

1. A catheter comprising:
   a shaft comprising a tubular element extending in a longitudinal direction from a proximal end of the shaft to a distal end of the shaft, and a plurality of ribs extending in the longitudinal direction along the tubular element, the tubular element having an outer surface, a plurality of attachment surfaces, and a catheter surface; and
   a balloon element fitted on the shaft and coupled to the plurality of attachment surfaces such that the balloon element has an inner surface area between the plurality of attachment surfaces;
   the plurality of ribs are positioned under the balloon element, each of the plurality of ribs comprising a peak and a balloon contact surface,
   each peak being rounded in a circumferential direction about an axis of the catheter extending in the longitudinal direction, and a radius of curvature of each peak is less than a radius of curvature of the shaft; and
   the tubular element comprising at least two surfaces which are attenuated relative to the balloon contact surfaces of the plurality of ribs such that a surface area of the shaft provided for contacting the inner surface area of the balloon element when deflated is less than the inner surface area of the balloon element when deflated, the balloon element contacting at least one of the balloon contact surfaces when deflated.

2. The catheter according to claim 1, wherein the tubular element comprises a liquid channel extending from the distal end of the shaft to the proximal end of the shaft.

3. The catheter according to claim 2, wherein the liquid channel terminates in eyelets at the proximal end of the shaft.

4. The catheter according to claim 1, wherein the number of the plurality of ribs is between 4 and 10.

5. The catheter according to claim 1, wherein the catheter is a Foley catheter.

6. The catheter according to claim 1, wherein the catheter is a rectal catheter.

7. The catheter according to claim 1, wherein the shaft includes between 6 and 16 ribs.

8. The catheter according to claim 1, wherein a transverse cross-section of the each of the plurality of ribs of the catheter forms part of a circular arc having a center at a periphery of the catheter.

9. The catheter according to claim 1, wherein the plurality of ribs are shorter than a distance between the plurality of attachment surfaces.

10. The catheter according to claim 1, wherein the shaft includes 8 ribs.

11. A catheter comprising:
a shaft having a proximal end, a distal end, and an outer surface, the shaft extending longitudinally along a length of the catheter, the shaft comprising:
a plurality of balloon attachment portions situated along the shaft, and
a plurality of ribs defining a plurality of troughs situated about the shaft and between the plurality of balloon attachment portions such that the shaft includes a plurality of lowered surfaces and a plurality of surfaces raised relative to the plurality of lowered surfaces between the plurality of balloon attachment portions; and
an inflatable balloon fitted over the shaft such that the balloon is supported by the plurality of raised surfaces and such that when deflated, the balloon contacts a portion of at least one of the raised surfaces and is prevented from contacting a portion of the plurality of lowered surfaces while draping into at least one of the plurality of troughs.

12. The catheter of claim 11, wherein the balloon is configured to transition between an inflated state and a deflated state.

13. The catheter of claim 12, wherein a fluid is deposited within the plurality of troughs such that the fluid is situated beneath the balloon, and wherein the fluid facilitates the transitioning of the balloon between the inflated and deflated states.

14. The catheter of claim 12, wherein the catheter further comprises a balloon channel having outlets situated between the plurality of attachment surfaces such that the outlets are beneath the balloon, the balloon channel facilitating a delivery of fluid to the plurality of troughs and a removal of fluid from the plurality of troughs for transitioning the balloon between inflated and deflated states.

15. The catheter of claim 11, wherein a contact surface area of the balloon is defined between the plurality of balloon attachment portions and configured for contacting the outer surface of the shaft, and wherein a surface area of the shaft configured to support the balloon between the plurality of balloon attachment portions is less than the contact surface area of the balloon.

16. The catheter of claim 11, wherein the shaft comprises a liquid channel extending from its proximal end to its distal end.

17. The catheter of claim 11, wherein the catheter is a Foley catheter.

18. The catheter of claim 11, wherein the catheter is a rectal catheter.

19. A catheter comprising:
a shaft comprising a tubular element extending in a longitudinal direction from a proximal end of the shaft to a distal end of the shaft, and a plurality of ribs extending in the longitudinal direction along the tubular element, the tubular element having an outer surface, a plurality of attachment surfaces, and a catheter surface; and
an inflatable balloon element fitted on the shaft and coupled to the plurality of attachment surfaces such that the balloon element has an inner surface area between the plurality of attachment surfaces; the plurality of ribs are positioned under the balloon element, each rib having a balloon contact surface;
at least two surfaces which are attenuated relative to the balloon contact surfaces of the plurality of ribs such that a surface area of the shaft provided for contacting the inner surface area of the balloon element when deflated is less than the inner surface area of the balloon element when deflated, the balloon element contacting the balloon contact surface of at least one of the plurality of ribs when deflated, the shaft also being provided with a balloon channel having outlets situated between the plurality of attachment surfaces such that the outlets are beneath the balloon element; and
a circumferential gap is adjacent one of the plurality of attachment surfaces such that the plurality of ribs partially extend between the plurality of attachment surfaces.

20. A catheter comprising:
a shaft having a proximal end, a distal end, and an outer surface, the shaft extending longitudinally along a length of the catheter, the shaft comprising:
a plurality of balloon attachment portions contact surfaces situated at circumferentially spaced positions about the shaft, and a plurality of ribs extending in the longitudinal direction along the shaft such that a transverse cross-section of the shaft defines a plurality of troughs and a plurality of raised surfaces, each trough having a bottom, each raised surface having a top, wherein the bottoms of the plurality of troughs define a circumference of the catheter; and
an inflatable balloon fitted over the shaft such that when the balloon is in a deflated state, the balloon is supported by contact with the tops of the plurality of raised surfaces and by contact with the bottom of at least one of the plurality of troughs where the balloon describes a tangent to the circumference of the catheter.

* * * * *